United States Patent [19]

Felblinger et al.

[11] Patent Number: 5,423,863
[45] Date of Patent: Jun. 13, 1995

[54] METHOD OF RECOGNIZING A VENTRICULAR CARDIAC PATHOLOGICAL CONDITION FOR AUTOMATIC DEFIBRILLATION PURPOSES, AND MONITOR-DEFIBRILLATOR FOR IMPLEMENTING SAID METHOD

[75] Inventors: Jacques Felblinger, Berne, Switzerland; Albert Cansell; Didier Meyer, both of Wissembourg, France

[73] Assignee: Odam, S.A., Wissembourg, France

[21] Appl. No.: 75,547

[22] PCT Filed: Dec. 13, 1991

[86] PCT No.: PCT/FR91/01011

§ 371 Date: Sep. 29, 1993

§ 102(e) Date: Sep. 29, 1993

[87] PCT Pub. No.: WO92/10805

PCT Pub. Date: Jun. 25, 1992

[30] Foreign Application Priority Data

Dec. 13, 1990 [FR] France .................. 90 15804

[51] Int. Cl.$^6$ .................. A61N 1/39
[52] U.S. Cl. .................. 607/5; 128/705
[58] Field of Search .................. 128/705; 607/5

[56] References Cited

U.S. PATENT DOCUMENTS

| | | | |
|---|---|---|---|
| 4,432,375 | 2/1984 | Angel et al. .................. | 128/705 |
| 4,453,551 | 6/1984 | Anderson et al. . | |
| 4,523,595 | 6/1985 | Zibell . | |
| 4,919,144 | 4/1990 | Vandehey .................. | 128/705 |
| 5,000,189 | 3/1991 | Throne et al. .................. | 128/705 |
| 5,077,667 | 12/1991 | Brown et al. .................. | 128/705 |
| 5,191,884 | 3/1993 | Gilli et al. .................. | 607/5 |

FOREIGN PATENT DOCUMENTS 2103913 4/1972 France .

OTHER PUBLICATIONS

"ECG/VCG Rhythm Diagnosis Using Statistical Signal Analysis-11. Identification of Transient Rhythms", vol. BME25, No. 4, Jul. 1978, By D. Gustafson et al., pp. 353-361.

"Medical Usage of an Expert System for Recognizing Chaos", vol. 10, No. 3, Nov. 1988, By K. Krantz et al., pp. 1303-1304.

"Detection of Ventricular Fibrillation by Sequential Testing", Sep. 1988, By Z. Yi-Sheng et al., pp. 325-328.

Primary Examiner—William E. Kamm
Attorney, Agent, or Firm—Young & Thompson

[57] ABSTRACT

Procedure to recognize a ventricular cardiac pathological condition in view of an automatic defibrillation and monitor/defibrillator to implement the procedure Procedure to recognize a ventricular cardiac pathological condition characterized in that after an analog pre-processing, the ECG signals are continuously sampled and digitized, then digitally processed by basic periods in such a manner as to periodically measure distinct basic values according to three criteria of zeros Z, of cardiac frequency FC and of arrythmia RR, then to individually allocate to each value a probability weighting according to a weighting scale specific to each criteria, to proceed to sum these basic values to establish an overall probability over a given duration utilized to determine the triggering of a recognition alarm of a cardiac pathological condition. The invention is of particular interest in cardiology in the medical industry.

10 Claims, 15 Drawing Sheets

METHOD OF RECOGNIZING A VENTRICULAR CARDIAC PATHOLOGICAL CONDITION FOR AUTOMATIC DEFIBRILLATION PURPOSES, AND MONITOR-DEFIBRILLATOR FOR IMPLEMENTING SAID METHOD

FIELD OF THE INVENTION

The present invention concerns a procedure to monitor, detect, and to automatically recognize a dangerous cardiac pathological condition in a patient such as a ventricular fibrillation or a ventricular tachycardia in order to sound an alarm and perform a semi-automatic defibrillation.

This invention also concerns means to implement the procedure as a monitor-detector-defibrillator.

BACKGROUND OF THE INVENTION

The monitoring of the cardiac activity is necessary in all serious pathological and cardiac cases and in all emergency cases inasmuch as the monitoring allows gathering of information on the momentary condition of the patient.

Additionally, the patients and sick susceptible to cardiac disturbances, and notably to disturbances in the cardiac rhythm, necessitate attentive monitoring depending on the seriousness of their condition.

Actually, arrhythmia generally leads to serious disturbances that may, in certain conditions, lead to the fibrillation of the myocardium, an extremely serious condition that only an electric defibrillation shock can modify.

A fibrillation corresponds to a total desynchronization of the excitation of the cardiac fibers, caused by excitation loops that close on themselves. A self-sustaining movement is created in these loops, called reentrant loops, preventing all new excitation of the cardiac muscle.

A local fibrillation in the auricles (auricular fibrillation) is not deadly and may be reduced by an electric shock.

Localized in the ventricles, this fibrillation (ventricular fibrillation) completely stops the functioning of the heart. Indeed, the mechanical contraction of the heart practically no longer occurs. This total hemodynamical ineffectiveness causes death in the three to five minutes following the onset of the disturbance because of a lack of cerebral irrigation. Only a defibrillation electric shock can resynchronize all of the cells of the heart.

This treatment consists in applying through the thorax, by two electrodes, a short duration current of a few tens of amperes at a few thousands of volts for a few milliseconds resulting from the discharge of a capacitor.

Since a few years ago, the defibrillators have been equipped with a cardiac monitor to visualize the signal of the electrocardiogram, abbreviated ECG, before and after the defibrillation shock.

Actually, ventricular fibrillation is responsible for most of the deaths occurring during the course of the pre-hospitalization phase of myocardial infarction, without rapid intervention and appropriate emergency equipment. Indeed, present arrhythmia detectors are complex, not transportable, and necessitate the presence of a physician to recognize the fibrillation pathology.

SUMMARY OF THE INVENTION

The first goal of the invention is thus to provide emergency equipment that is simple, autonomous, and light, which consumes little energy and is capable of detecting and automatically recognizing a ventricular fibrillation condition in view of sounding an alarm, thus rendering the presence of a physician non-indispensable for the recognition of fibrillation.

Another goal is to extend the recognition to other hazardous pathologies such as ventricular tachycardia where the cardiac frequency is greater than 140 beats per minute, which presents recognition criteria is common with those of fibrillation and also necessitates an electric shock for its treatment.

In this manner, one of the goals of the present invention consists in proposing a monitor-detector capable of recognizing ventricular fibrillation as well as ventricular tachycardia.

A related goal of the invention is the ability to deliver QRS complex detection data correctly synchronized with the electrocardiogram due to the importance of the timing of the electric shock for ventricular tachycardia.

Another goal of the invention concerns the possibility, as soon as the alarm is sounded, to be able to prepare the electric shock and to propose a decision to shock, which means placing the associated emergency defibrillator in condition to deliver the shock as soon as the operator validates the proposal, thereby notably shortening the intervention delay.

Yet another goal of the invention concerns the possibility of an automatic defibrillation decision after an additional analysis.

An additional goal of the invention is the ability to function in real-time.

The last goal specified consists in conceiving a monitor-detector whose functioning must produce the fewest false negatives corresponding to missing detections and the fewest false positives corresponding to excessive detections.

To attain all of these goals, it was necessary to identify and resolve many difficulties in the automatic detection of fibrillation and ventricular tachycardia, to remedy them and to conceive an entire procedure for the analysis and recognition of the pathology starting from the electrocardiogram signals.

Notably, it was necessary to overcome the following significant difficulties:
  research and study the choice of the analysis and recognition criteria;
  eliminate or minimize all of the parasitic signals hindering detection and identification such as the induced, interfering or associated equipment coupling signals, background noise, line noise, ambient radio frequency noise and stimulation impulses;
  creating an analysis and recognition computer;
  establishing, for each criterium, an increasing probability scale.

To this effect, the present invention concerns a procedure to monitor, to detect and to identify, from an electrocardiological signal, a condition of ventricular fibrillation or rapid ventricular tachycardia, characterized in that after analog preprocessing, the ECG signals are continuously sampled and digitized, then digitally processed in basic periods to provide a periodic measurement of individual basic values according to the three criteria of zeros Z, cardiac frequency FC and arrhythmia RR, then to individually allocate to each value a probability weighting according to a weighting scale specific to each criterium, to proceed with the summation of these values to establish a basic probability linked to a basic period of analysis and to use the basic probability of a basic period of analysis and measurement to join it to the preceding probability in such a manner as to establish an overall probability used to determine the triggering of a recognition alarm of a pathological cardiac condition.

BRIEF DESCRIPTION OF THE DRAWINGS

The technical characteristics and other advantages of the invention are consigned in the following description, given as example only and not limited by a specific embodiment in reference to the accompanying drawings, in which.

DESCRIPTION OF THE PREFERRED EMBODIMENTS

Preliminary to the detailed description of the present invention, we will now clarify the different concepts and definitions useful for a clear and good understanding of the description made hereafter.

The electrocardiographic signal transduced by a electrocardiogram, abbreviated ECG is sensed from the body of the patient by external electrodes in contact with the skin. If the defibrillation electrodes are adhesive, they may be used to sense the ECG signal.

Figure 1:
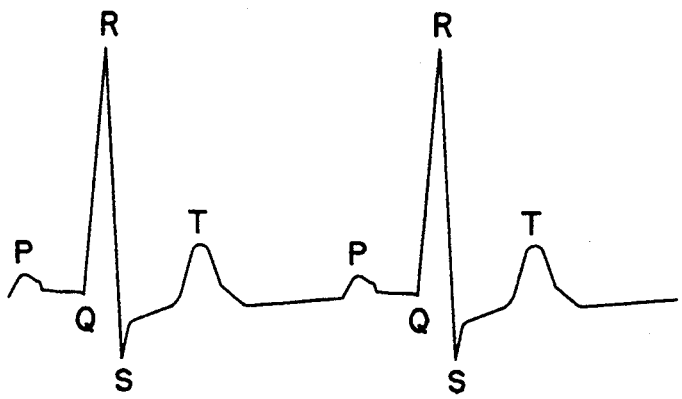
FIG. 1 is an enlarged waveform of an electrocardiogram.
Figure 2:
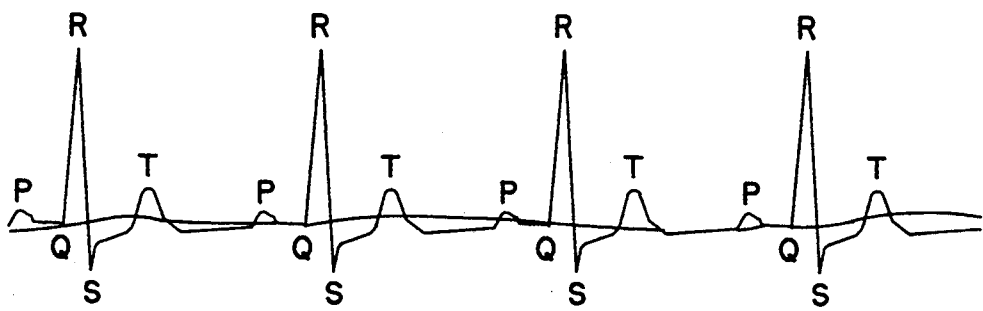
FIG. 2 is a normal electrocardiogram, meaning a waveform of electrocardiographical signals in the case of normal cardiac activity.
Figure 3:
FIG. 3 is a normal electrocardiogram showing waveforms corresponding to extra systoles.

The electrocardiographic signals of a healthy heart during normal activity are repetitive and display a known repetitive waveform constituted by several segments whose characteristic points are conventionally called P, Q, R, S and T, which are represented in FIG. 1.

The wave P corresponds to the depolarization of the auricles. The interval PQ represents the auriculo-ventricular conduction time. The QRS complex corresponds to the ventricular depolarization (propagation in the ventricles). The repolarization of the ventricles happens from S to T (segment ST) and during the wave T.

The QRS complex is one of the characteristic elements of an electrocardiogram of normal cardiac activity. It will be used in the procedure described hereinafter.

Synchro impulse QRS

The term "synchro impulse QRS" designates the impulse formed from the real QRS complex by comparison with a threshold of fixed or variable value, for example variable in the case of the application envisioned here.

Its role consists in showing the existence of a QRS complex or of a very similar neighboring waveform.

In addition, it constitutes a temporal reference for the triggering of the defibrillation shock in case of ventricular tachycardia.

Interbeating

The term "interbeating", abbreviated "Ti", is attributed to the duration separating two synchro QRS impulses.

PACE

By convention, the term PACE signifies the inhibition of the stimulation impulse.

Figure 4:
FIG. 4 is an electrocardiogram of a ventricular fibrillation condition.
Figure 5:
FIG. 5 is an electrocardiogram of ventricular tachycardia.

As it appears in the electrocardiograms represented in FIGS. 4 and 5, the electrocardiogram signals characteristic of fibrillation and ventricular tachycardia reveal themselves by a complete loss of the reproducible and periodic characteristic.

In regard to the fibrillation, the arrhythmic and random appearance of the signal is to be noted.

In contrast, ventricular tachycardia ECG signals show a high frequency pseudo-periodicity.

The procedure to monitor, to detect and to recognize a ventricular fibrillation or ventricular tachycardia condition from a electrocardiographic signal according to the invention follows from the general inventive idea consisting of preprocessing, digitizing the electrocardiographic signals after a division according to a predetermined frequency, measuring from these signals values corresponding to the three criteria of zero, of cardiac frequency, of arrhythmia, periodically allocating variable probability parameters to these values representative of these three criteria, as a function of their levels taken from the weighting scale specific to each criteria during two consecutive elementary analysis periods and making the measurements on each basic period correspond to a basic probability by the weighting scales, each basic probability of each period being added to the preceding one to form an overall probability as a function of these criteria to recognize, according to a given probability factor, a hazardous pathological condition and to trigger an alarm.

The procedure may be carried out by an additional criteria specific to ventricular tachycardia.

After a conventional acquisition phase, carried out by conventional monitors, the ECG signals undergo an analog preprocessing by a filtering in a 1–40 Hz bandpass filter with suppression of the DC component. This filtering essentially rids signals of parasitics and harmonic components hindering the processing of the signals. The filtering is followed by an automatic gain control AGC in such a manner as to always present the ECG signal to the analog to digital converter ADC at full scale.

The analog signals are then sampled and converted into digital signals in the ADC at a sampling frequency of 250 Hz during an overall analysis of duration D, for example 8 seconds, formed by two successive sampling and analysis basic periods TA and TB, for example, of a duration of 4 seconds each, thus corresponding to 1.000 samples each. The automatic gain control AGC is an optimal analysis of the maximum value, whose goal is to always use the full scale of the converter when carrying out the digital signal conversion step.

It is to be understood that by automatic gain control, abbreviated AGC, connected to the analog/digital converter ADC, an operation is meant which consists in using the maximum amplitude of the EGC signal as a full scale value of the converter.

In this manner, whatever the maximum amplitude of the ECG signal may be, the same maximum digital value (full scale) will be used to have a usable signal available in all cases.

Everything happens just as if the converter was adapting itself to the amplitude of the ECG signal.

For example, a QRS amplitude of 2 volts will be decomposed into 256 equidistant levels, and 2 volts will correspond to the full digital scale. According to the targeted automatic gain control, a maximum QRS amplitude of 2 volts will have the same maximum digital value as a maximum amplitude of 1 volt, the intervening values undergoing a proportional conversion.

Moreover, it is known that the preprocessed ECG analog signal has a usual amplitude situated, according to the patient, between 0.2 mV and 5 mV. It is also known that for the small amplitudes around 0.2 mV, the ECG signal is not adequately usable. It is necessary to allow for an inhibition signal of the detector, abbreviated LIMIT in FIG. 20, which validates the alarm, thus signalling the non-possibility of detection.

Concurrently with the analog preprocessing and the digitization, the analog signals output from the acquisition stage undergo a detection of the "QRS" complex in view of forming the synchro QRS impulse, as will be described hereinafter.

Formation of the Synchro Impulse

Figure 21:
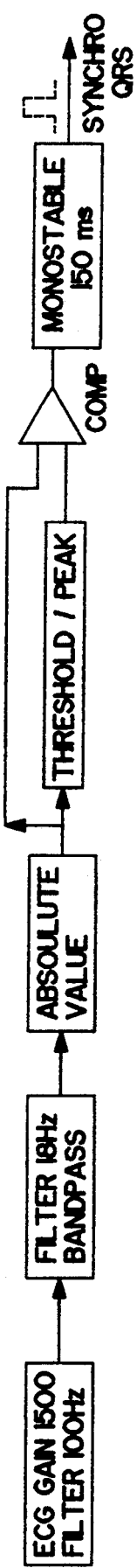
FIG. 21 is the diagram of the principle of the detector of the QRS complexes and the formation of the synchro QRS impulse.

The synchro QRS impulse is formed by a QRS detector constituted by the following modules represented in FIG. 21:

DESCRIPTION

| DESCRIPTION | FIG. 21 LABEL |
| --- | --- |
| frequency of 100 HZ and a gain of 1.500 | FILTER GAIN 100 Hz |
| bandpass filter centered on 18 Hz | BANDPASS 6 Hz |
| absolute value module | ABSOLUTE VALUE |
| threshold/peak module | THRESHOLD/PEAK |
| comparator module | COMP |
| impulse trigger | MONOSTABLE |

The QRS complex detector is based on the analysis of the response of a bandpass filter of 18 Hz of width 6 Hz. It is the absolute value of the signal that is analyzed. If this absolute value exceeds a threshold that is a function of the peak amplitude of the last QRS complex and a fixed threshold, a synchro QRS impulse is emitted indicating by its presence that the QRS complex is recognized.

In this manner, the presence of the synchro QRS impulses evidences the existence of the QRS complex in the ECG signal analyzed.

The digital signals output from the analog and digital preprocessing stage and from the QRS detection stage are processed in a digital processing unit which consists in various steps, of calculation and digital analysis stages with respect to certain predetermined criteria and variable according to specific sequences described hereinafter, analyses which lead to the recognition of a hazardous pathological condition according to a given probability, determined by said criteria but modifiable, and to the manual or automatic triggering of an alarm.

The selection of the criteria usable for the recognition of hazardous cardiac pathological condition results from much effort and many trials.

To recognize a ventricular fibrillation condition, the method and the utilized selected criteria are outlined hereinafter:

- the analysis is carried out on samples of duration D decomposed in two juxtaposed successive periods TA and TB of 4 seconds each;
- the three essential criteria are: a criterium "of zeros", a criterium of "cardiac frequency" FC, and a criterium "of arrythmia" RR;
- a rapid ventricular tachycardia criterium is added to increase the sensitivity and the reliability of the detection for this cardiac pathology;
- the definition of these criteria are such that they are not uniquely TRUE or FALSE but may have intermediate states.

After a basic analysis period TA or TB, for example 4 seconds, the value of the basic probability worked out over this period of a ventricular fibrillation case PFV is incremented by adding the basic probability of the immediately preceding period APFV to determine an overall probability linked to the duration D of two juxtaposed analysis periods TA and TB. This overall probability: PGV=PFV+APFV is used to trigger the alarm.

To avoid abnormally short sequence or artifacts, it is the sum of this ventricular fibrillation probability PFV and the immediately preceding ventricular fibrillation probability APFV calculated over the preceding period TA which will determine the triggering of the alarm.

To properly understand the following, the three criteria used, meaning criterium of zeros Z, criterium of cardiac frequency FC, criterium of arrythmia RR and a fourth optional criterium, with the aide of FIGS. 9 to 14 will now be defined in a simple manner.

1. The Criterium of Zeros "Z"

The selection of this criterium was guided by the following considerations.

The statistical study of normal cardiac activity has allowed us to notice that, in an ECG, 60% of the points are located at a level below the + or −20% of the maximum value of the normal ECG (see FIG. 9). The counting of all of these signals gives an idea of the morphology of the signal.

This criterium has been further improved in the following manner:
- the maximum of the digital ECG always corresponds to the full scale of the conversion thanks to the automatic gain control AGC;
- a threshold established at + or −20% of the maximum allows the suppression of noise for the signals of weak amplitudes and strongly attenuates the effect of parasitic signals, telephonic waves and radioelectric waves;
- a lower limit (for example of 0.2 mV), under which no processing may be made, validates the detection;
- this criterium is not true or false but takes in consideration a certain number of values as a function of the number of zeros counted, these values having been statistically defined.

With over 70% of the values close to zero, the probability of having a normal ECG is null. From 70 to 50%, the morphology is different from a normal sinusoidal rhythm and an emergency condition is probable. Under 50%, the probability is high.

The criterium of zeros implements the counting of the number of sampled points whose level is close to zero. The sampled points that are called close to zero are those whose value is less than + or −20% of the maximum of the ECG, because in the case of ventricular fibrillation FV and ventricular tachycardia TV, the number of points close to zero becomes low.

Figure 9:
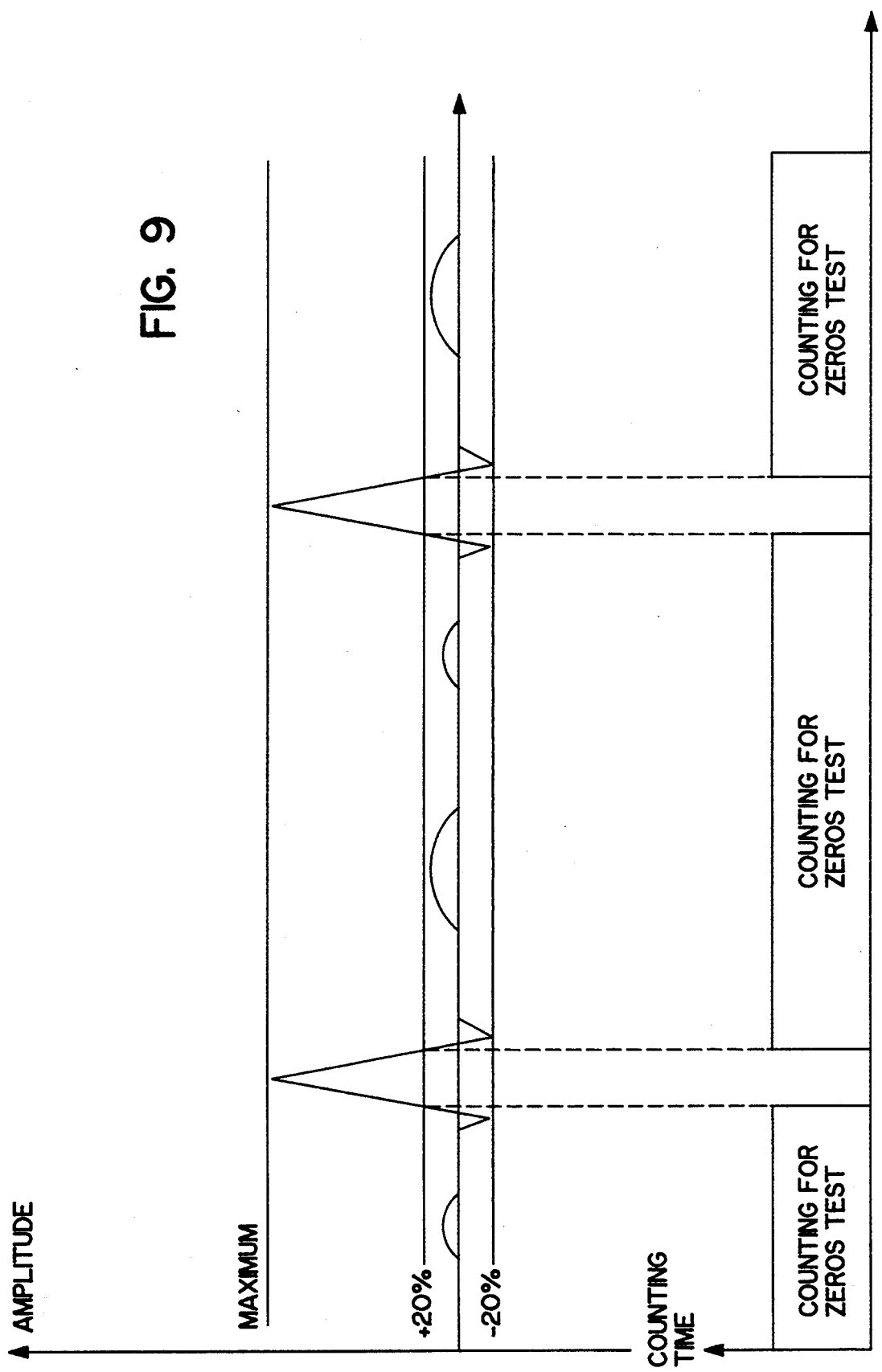
FIG. 9 is a double graphic explaining the analysis criterium called "zero criterium"

The criterium of zeros is precisely and mathematically defined in the following manner:

It relates to the percentage of the number of sampled points during a basic analysis period, whose voltage level is situated at + or −20% of the maximum voltage level of the ECG relative to the total number of sampled points that are less than 50% of the total number (FIG. 9).

This value is defined by Z.

The zero criterium gives an idea of the width of the QRS complex.

Example normal ECG: a Z value greater than 60% is found';
TV and FV correspond to a Z value less than 50%.

2. The cardiac frequency criterium "FC"

Figure 10:
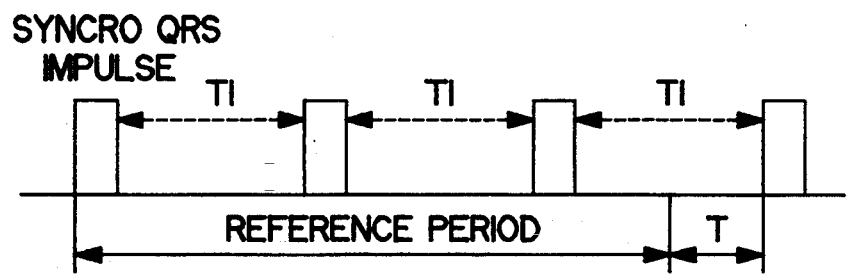
FIG. 10 is a diagram illustrating the definition of the criterium of the cardiac frequency FC.

It principally concerns ventricular tachycardias.
It is defined by the following formula:

$$FC = 60 \times (N+1)/(T+2)$$

where
- N = number of synchro QRS impulses counted during a reference period;
- T = duration between the end of the reference period and the next synchro QRS impulse (FIG. 10).

Application example of the formula:

Three synchro impulses are counted during two seconds (reference period) and the next synchro impulse arrives after one second.

N = 3 and T = 1

By applying the above formulation, it is found that:
FC = 80 beats per minute

This cardiac frequency is to be compared with an actual cardiac frequency of 80 beats per minute. In principle, this calculated cardiac frequency is equal to the actual cardiac frequency.

Although it is difficult to define a threshold under which an alarm must sound, the increasing probability scale is the following:
- from 150 to 200 b/mn the probability is low
- from 200 to 300 b/mn, it increases;
- beyond 300 b/mn, it is greatest.

3. The arrythmia criterium "RR"

The arrythmia criterium is evidenced by a degree of arrythmia RR.

It characterizes the random phenomena of ventricular fibrillation, the other cardiac rhythms being fairly regular.

Figure 12:
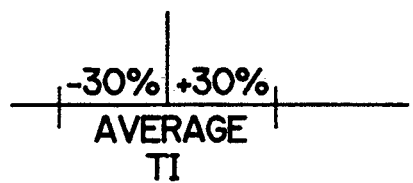
FIG. 12 is a diagram illustrating the definition of the analysis criterium called "arrhythmia criterium"
Figure 11:
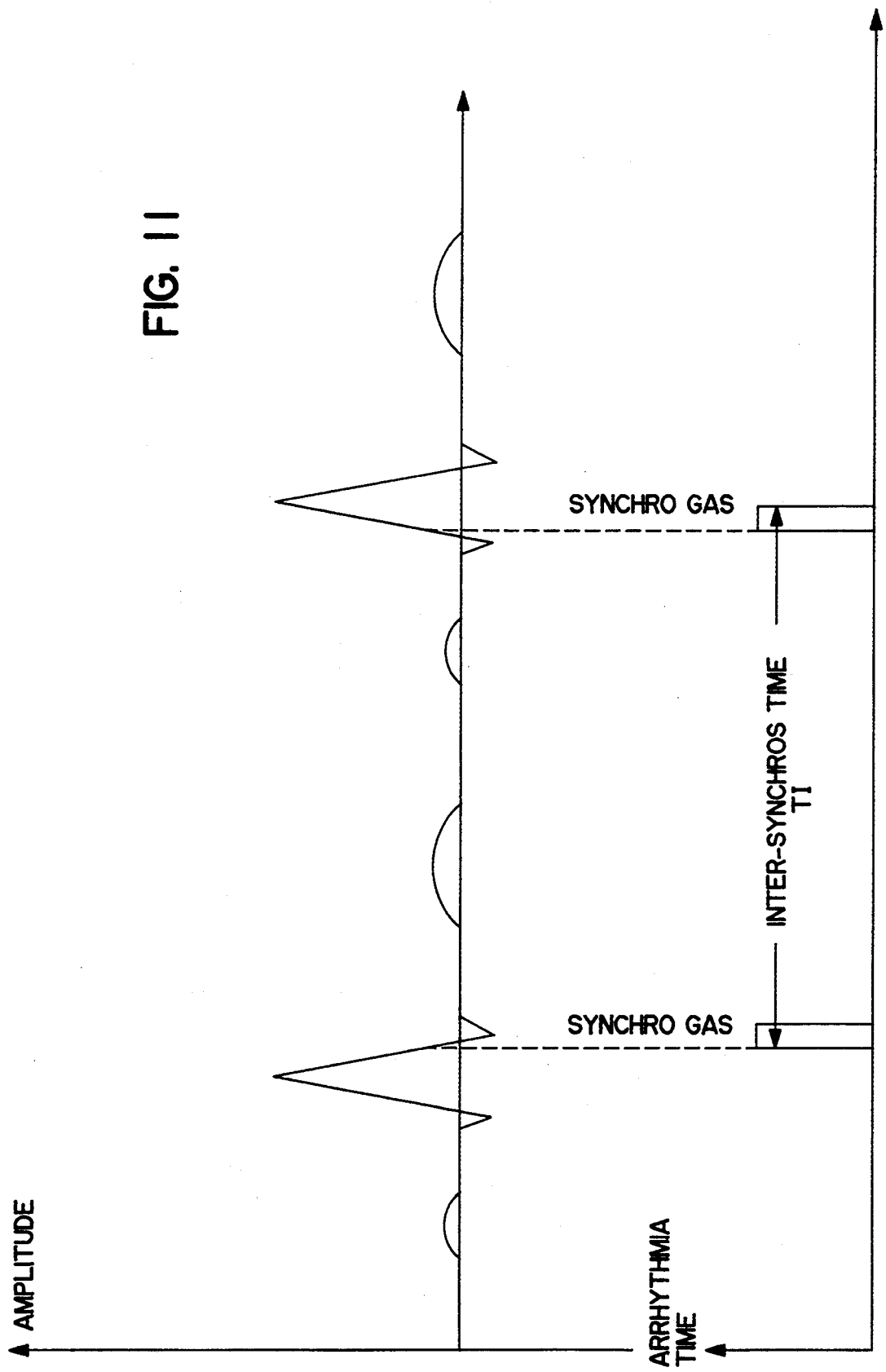
FIG. 11 is a double graphic showing the position of the synchro QRS impulses to implement the analysis criterium called "arrhythmia criterium"

The degree of arrythmia is defined as the relationship in percentage of the number of interbeatings out of ten from the last ten interbeatings whose relative value are located at or −30% of the average interbeating value, abbreviated "average Ti" (FIG. 12).

Examples

The Ventricular Fibrillation FV

It is characterized by an irregular signal. If the arrythmia signal is weak, for example greatly inferior to 50%, it will engender a high coefficient of ventricular fibrillation probability PFV.

The Ventricular Tachycardia

It is characterized by a regular signal. If the degree of arrythmia is high, for example greater than 50%, it will engender a low coefficient of ventricular fibrillation probability PFV and conversely a high probability of ventricular tachycardia.

This criterium allows the discrimination of ventricular fibrillation from its essentially random character with respect to other cardiac frequency pathologies, of fairly regular nature.

4. The fourth criterium "PTV"

To increase the sensitivity of the detector for rapid ventricular tachycardia, a fourth criterium is provided for an improved embodiment.

According to this criterium, the three following conditions must be simultaneously satisfied:
- criterium of zeros "Z" less than 50%;
- cardiac frequency greater than 140 b/mn;
- degree of arrythmia RR greater than 75%;

These three conditions are systematically satisfied for the rapid ventricular tachycardia that is sought to be detected.

This criterium is implemented by the fourth test. It is totally transparent to the ventricular fibrillation which presents other typical characteristics.

This test leads to increasing the probability of a certain weight for rapid ventricular tachycardia.

To utilize another temporal reference, the analysis of the arrythmia is done at the end of four seconds and over the ten last intervals separating the two successive synchro QRS signals, these intervals being called "interbeating time" or Ti.

After having calculated the average of these times Ti, each interbeating is analyzed and compared to the average. A tolerance of 30% around this average determines the number of times Ti that are close to the average, this number corresponds to the degree or criterium of arrythmia.

Statistically, with eight out of ten interbeating intervals around 30% of the average, the rhythm is considered as regular, below that, the rhythm is irregular and may correspond to an emergency condition.

For this criterium, the auricular fibrillations have a large coefficient but do not trigger alarms, these conditions are thus not taken into account by the detector according to the invention.

The ECG signals that are sampled and digitized over a total duration D of two consecutive sampling and analysis periods are numerically processed in a microprocessor utilized as a microcalculator according to the chosen criteria earlier mentioned, of zero Z, of cardiac frequency FC, of arrythmia RR and for the improved embodiment according to a specific criteria of ventricular tachycardia PTV.

The 1.000 samples of each basic successive period TA and TB of 4 seconds each are accounted for and analyzed at the end of each period with respect to the chosen criteria.

Therefore:
a value "Z" is detected to be utilized by the test of the zeros;
the value "FC" representative of the cardiac frequency is worked out;
the value "RR" representative of the arrythmia is calculated;
each measurement value over a basic period is periodically attributed a weighting given by a weighting scale specific to each test to form a basic probability;
the basic probabilities are added over two successive analysis periods TA and TB to find a deciding overall probability linked to an analysis duration which will trigger or not the alarm according to its position with respect to a predetermined threshold.

The recognition of a ventricular fibrillation or ventricular tachycardia condition is continuously carried out from the analysis of the three criteria or of the four criteria (improved embodiment) over the total duration of analysis, eight seconds as in the example. It is agreed that if the overall probability PFG or PFVG (improved embodiment) of PFV and APFV is greater than 11, the ventricular fibrillation or ventricular tachycardia state is recognized by the microcontroller and an alarm is triggered.

However, 10 synchros are necessary to detect an emergency physiological condition.

Figure 19:
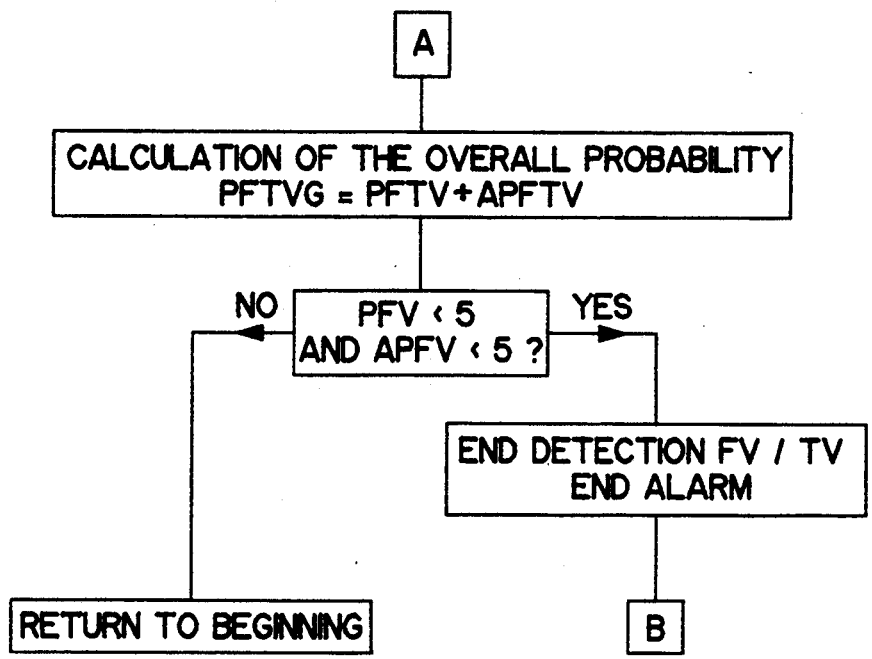
FIG. 19 is the flow chart continued from the algorithm according to the basic embodiment improved with four tests when there is an alarm or a detection in progress.

The end of the detection is obtained for two successive values less than 5 and the alarm stops (FIG. 19).

The procedure may be further carried out by an additional stage which consists in a stage of "shock proposal" which is evidenced by the charging of the defibrillation capacitors and the preparation of the equipment which delivers the defibrillation electric shock so the operator may intervene even more rapidly on the patient.

Figure 8:
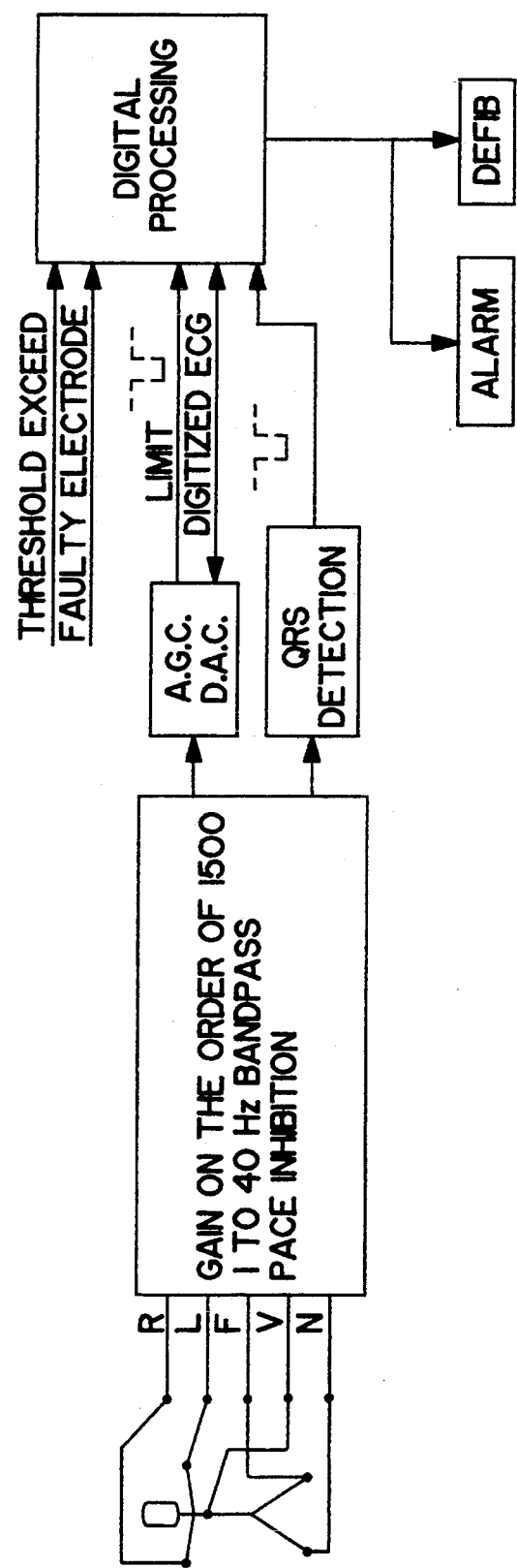
FIG. 8 is the synoptic diagram of the procedure to detect a hazardous pathological cardiac condition according to an embodiment without acquisition circuit.

According to another embodiment of the procedure, the preprocessing stage may be cancelled inasmuch as the acquisition stage of the ECG already delivers an adapted bandpass signal (FIG. 8).

An example will be given hereinafter of the weighting scales of the test utilized as well as a description of the functioning in the two conditions of fibrillation and ventricular tachycardia.

Figure 13:
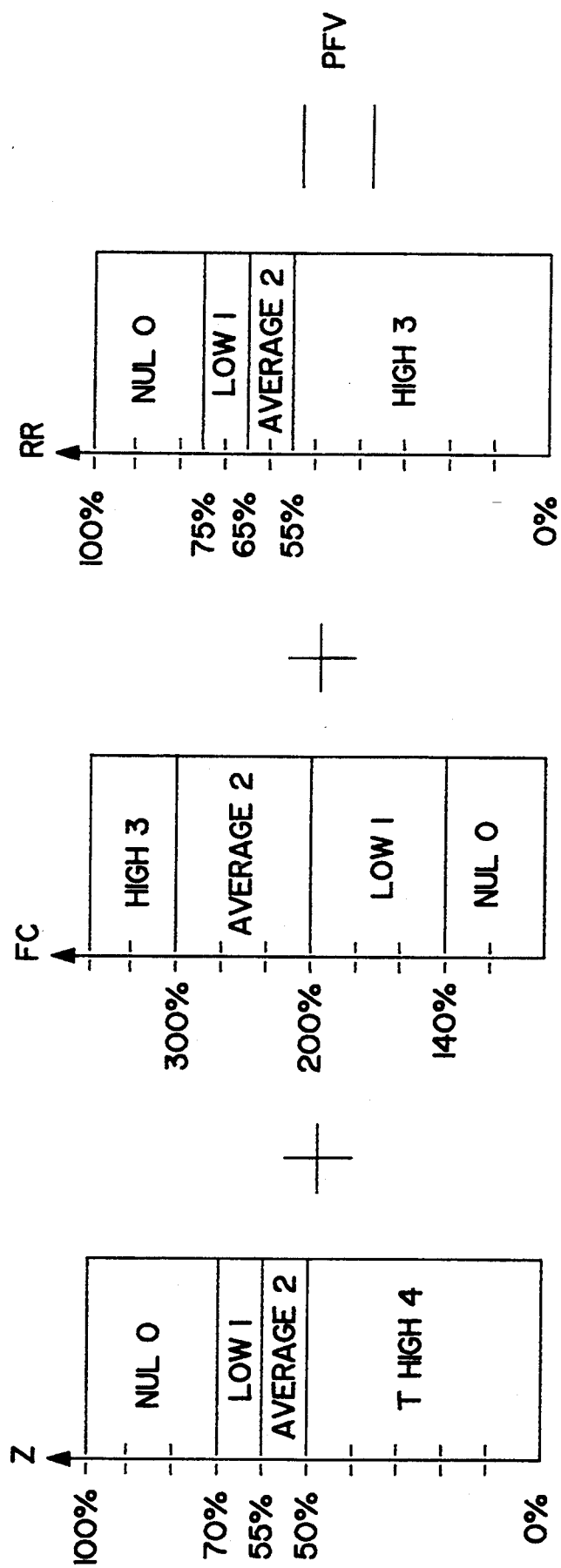
FIG. 13 is a composite diagram showing the weighting scales associated with the three principal tests.
Figure 14:
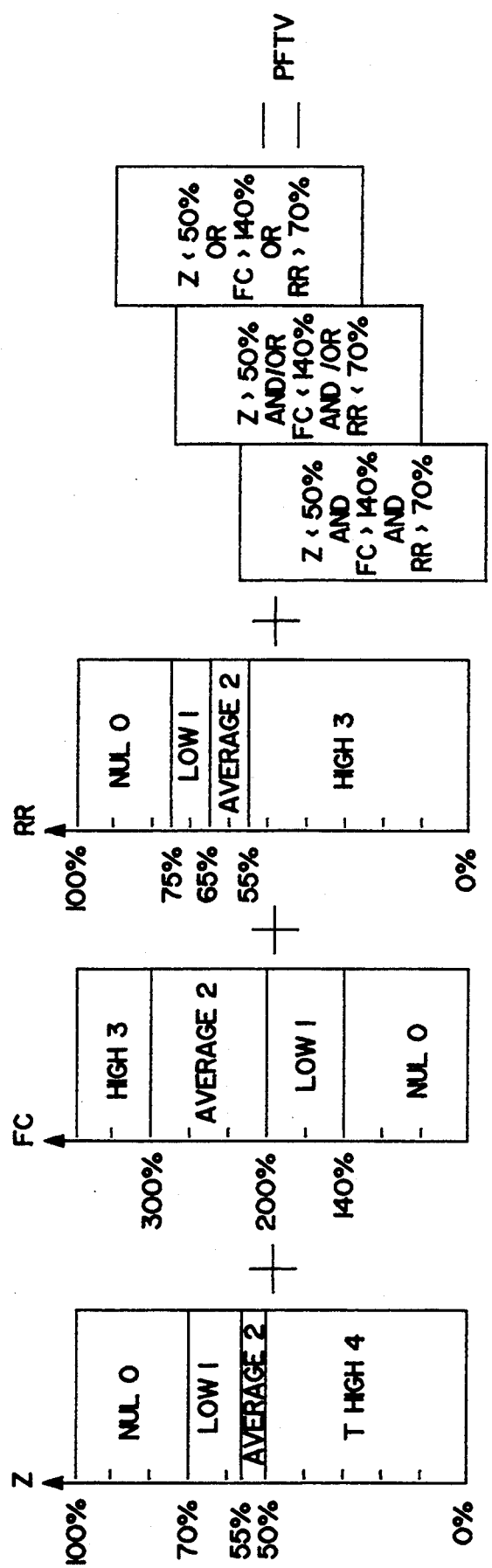
FIG. 14 is a composite diagram showing the weighting scales associated with the four tests of the improved procedure.

The FIGS. 13 and 14 illustrate the weighting scales of the tests used in the two embodiments of the procedure, which are, as already indicated, the following: test of zero (abbreviated: zero test), cardiac frequency test (abbreviated: FC test), arrythmia test (abbreviated: RR test) and according to an improved embodiment an additional test of the ventricular tachycardia probability (abbreviated: PTV test).

The goal of these figures is to clearly show the weighting coefficients attributed to the different values according to their level to determine a ventricular fibrillation probability PFV, after two successive analysis periods TA and TB, the immediately preceding analysis period probability being determined in the same manner and referenced by a APFV.

For each test, a weighting coefficient is allocated, according to the amplitude zone where the result of the weighting scale of this test is found.

Test of the Zeroes

The value of the probability is attributed, by the weighting scale of the test of the zeros, a variable weighting coefficient equal for example to:
4 if the number Z during the analysis period is located between 0% and 50%;
2 if the number Z during the analysis period is located between 50% and 55%;
1 if the number Z during the analysis period is located between 55% and 70%;
0 if the number Z during the analysis period is located between 70% and 100%;
3 beyond that period.

Cardiac Frequency Test FC

The value of the probability is attributed, by the weighting scale of the cardiac frequency FC test, a variable weighting coefficient equal for example to:
0 if the cardiac frequency during an analysis period is less than 140 b/mn (null probability);
1 if the cardiac frequency during the analysis period is located between 140 and 200 b/mn (low probability);
2 if the cardiac frequency during the analysis period is located between 200 and 300 b/mn (average probability);
3 beyond (high probability).

Arrythmia Test RR

The value representing the probability is attributed, by the weighting scale of the arrythmia test RR, a variable weighting coefficient equal for example to:
3 if the degree of arrythmia during the analysis period is less than or equal to 50%;
2 if the degree of arrythmia during the analysis period is located between 55% and 65%;

1 if the degree of arrythmia during the period of analysis is located between 65% and 75%;

0 if the degree of arrythmia during the period of analysis is located between 75% and 100%.

To avoid being limited by the specified numbers, it could as well be said that in such or such zone of values, the probability is null, low, average or large.

Fourth Test "PTV"

To increase the sensitivity and the reliability of the detection in the case of ventricular tachycardia, an additional test is carried out said ventricular tachycardia probability test (PTV) (FIG. 14).

This additional test consists in systematically verifying if the three following conditions are simultaneously satisfied:

few zero values denominated Z;

regular cardiac frequency determined by a low RR value;

the cardiac frequency is greater than 140 beats per minute.

If these conditions are not simultaneously met, the probability of zero is increased (the test is transparent). This is in the case of ventricular fibrillation.

Figure 18:
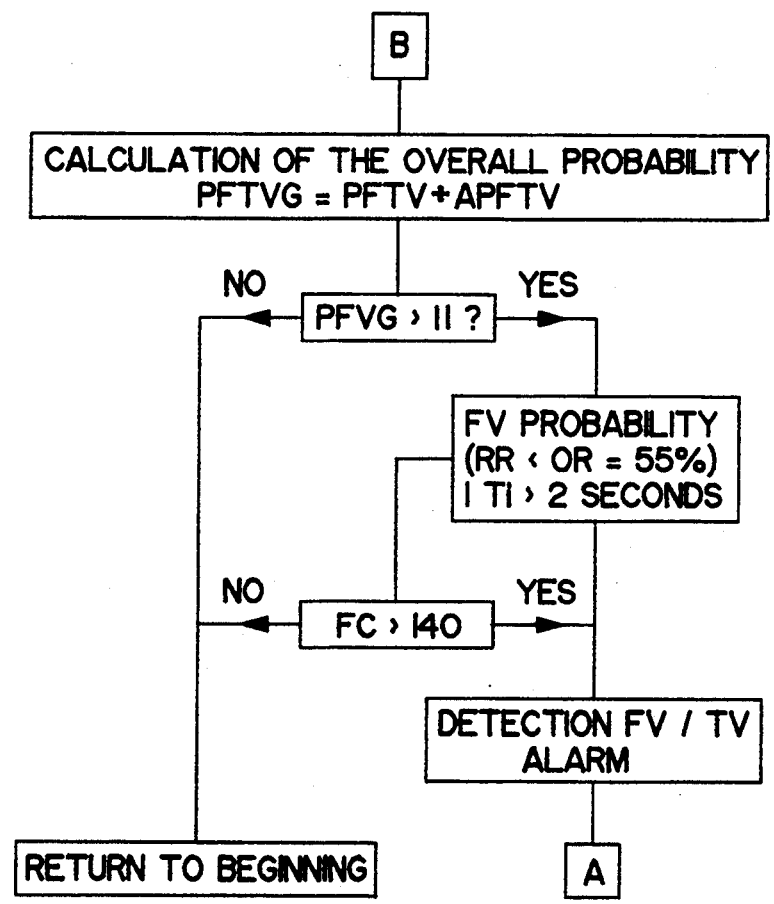
FIG. 18 is the flow chart continued from the algorithm according to the basic embodiment improved with four tests when there is no alarm or detection in progress.

If these conditions are simultaneously met, the basic probability is increased by a low weight (for example 1) to generate a new overall probability PFTVG=PFTV+APFTV (FIGS. 14, 18 and 19).

If necessary, a new limit of the probability causing the triggering of the alarm may be determined by increasing it for example by one unit.

For a better comprehension of the procedure of the implementing equipment, an example of detection of ventricular fibrillation and an example of detection of ventricular tachycardia using the improved embodiment (threshold of probability equal to 11) will be described hereinafter.

A pathological state is assumed to occur after several minutes of normal activity of the heart of the patient.

Ventricular Fibrillation

The sudden change in the nature of the signals is immediately evidenced by irregular synchro QRS impulses.

The test of the zeroes causes the weighting of this criterium to transition from a value of 0 to a value of 4 due to the larger waveforms.

The FC test will cause the value to exceed 200 beats per minute or in certain cases no QRS complex impulse will be generated during a duration necessarily greater than 2 seconds.

The RR test allocates a maximum weighting value because of the random character of the responses of the QRS detector.

A probability value for an analysis period will result from this test of PFTV+APFTV=9 for example, this sum becoming equal to 18 upon adding the weighting value from the next basic analysis period TA or TB. If this probability is greater than 11, a ventricular fibrillation condition FV will be recognized.

Rapid Ventricular Tachycardia

The change of the ECG signals to a typical deformation and an accelerated tachycardia rhythm is evidenced by a rapid rhythm with large QRS complexes.

This detection has been voluntarily limited to a rhythm greater than 140 beats per minute because the danger only appears above this heart rate.

In this manner, if this frequency is reached, the detector will react in the following manner.

The criterium of zeros will allocate a weighting value of 4 due to the large QRS complexes.

The criterium FC will contribute a weighting value of at least 1.

The criterium RR will not contribute any increase in the probability.

To trigger the alarm, it is the additional test of ventricular tachycardia probability PTV that will add a value equal to 1 if all of the conditions of this test are met.

The number of the overall probability will be equal to 6 for a first basic analysis period TA and equal to double that value, meaning PFV+APFV=12 after the second basic period TB.

According to the probability threshold established at 11, this number 12 being greater than 11, the alarm will sound.

From the digitized ECG signal, the magnitudes Z, FC and RR are established corresponding to the three criteria, meaning in conformity with the definitions specified hereinafter.

Z Magnitude

The magnitude Z to be used with the zero test is established by a comparison, followed by a counting of all of the sampled points whose voltage value corresponds to the value of the definition of the zero criteria, meaning two whose voltage level is located at + or −20% of the maximum voltage level of the ECG relative to the total number of sampled points.

Comparative measures allow the isolation of the number of points defined above; it is then necessary to give it the relative desired value corresponding to its definition.

These operations are carried out in the digital and calculation processing unit.

This magnitude is then put to the zero test according to the weighting scale corresponding to this criterium represented in FIGS. 13 and 14 to establish a basic probability according to the general algorithm.

Magnitude FC

This magnitude FC to be used with the cardiac frequency test is worked out by counting the number N of synchro QRS impulses during a given reference period. The duration T between the end of the reference period and the next synchro QRS impulse is accounted for as well.

The calculator establishes the cardiac frequency according to the formula:

$$FC = 60 \times (N+1)/(T+2)$$

This magnitude is then put to the cardiac frequency test according to the weighting scale specific to this criterium represented in FIGS. 13 and 14 to establish a basic probability according to the general algorithm.

Magnitude RR

This magnitude RR representing the degree of arrythmia corresponds to the definition specified hereinafter.

Ten interbeatings Ti are counted from the synchro QRS impulse. The average of these ten last interbeatings is calculated. The number of interbeatings are counted whose value is located at + or −30% of the average and the percentage of this number of interbeatings is calculated with respect to the total number of these interbeatings Ti over the period of calculation. By definition, this number is equal to ten.

This magnitude is then put to the arrythmia test according to a weighting scale specific to this criterium represented in FIGS. 13 and 14 to establish a basic probability according to the general algorithm.

General Algorithm

The general algorithm accounts for all of the contemplated tests and of the final algorithm intended for the taking of the decision.

This algorithm is represented in FIGS. 16, 17, 18 and 19.

It is described almost completely at all of the basic periods TA or TB.

Figure 15:
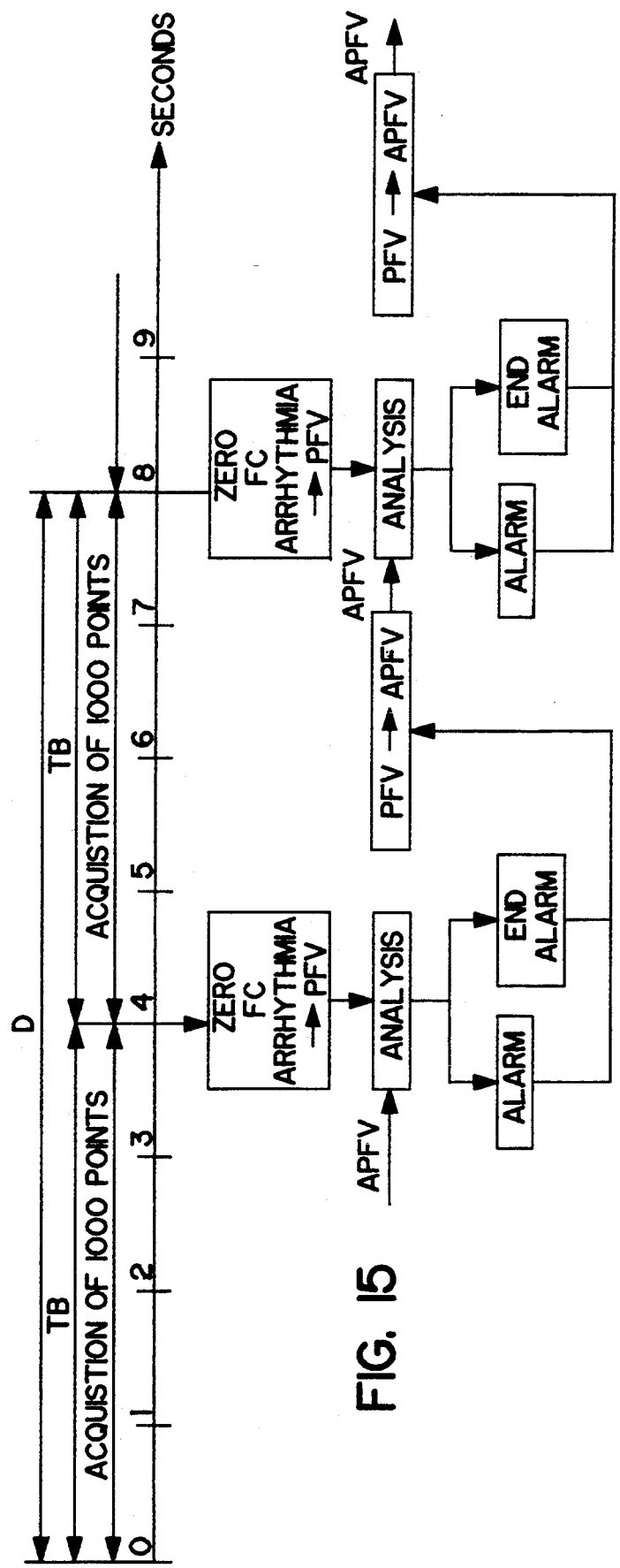
FIG. 15 is the diagram illustrating the chronology of the events over a period of analysis and measurement formed by the two successive and juxtaposed basic periods TA and TB.
Figure 16:
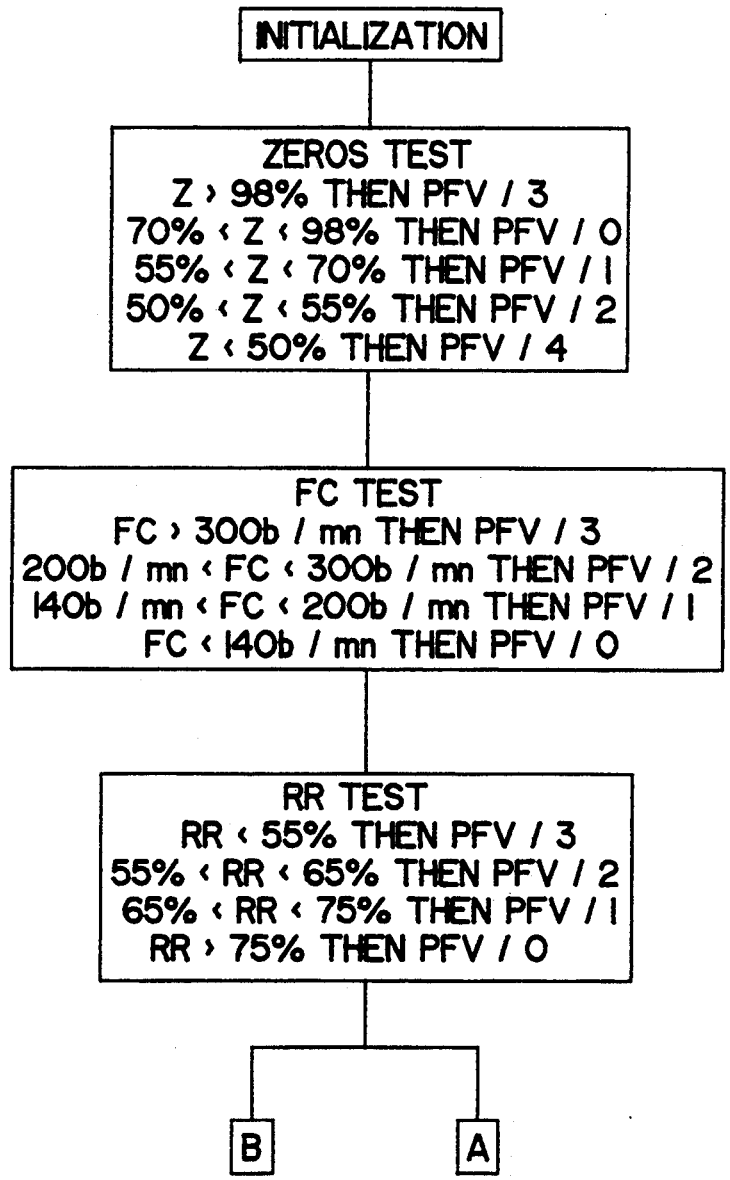
FIG. 16 is the flow chart of the algorithm of the three successive principal tests of the procedure according to the invention.
Figure 17:
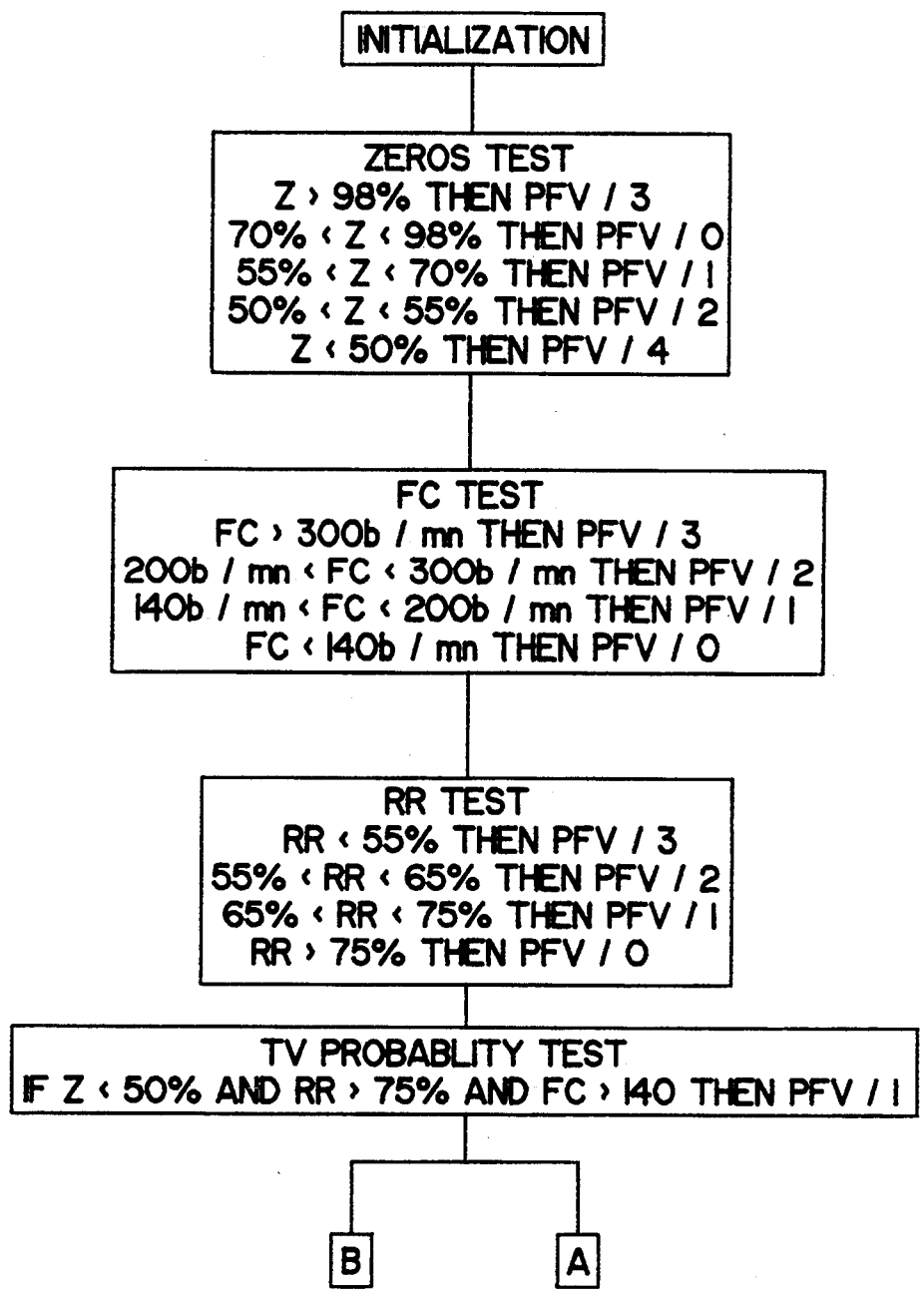
FIG. 17 is the flow chart of the logarithm of the four successive tests of the improved procedure according to the invention.

For a proper understanding, it is necessary to refer to FIG. 15.

This algorithm accounts for the progress of the systematic operations of the procedure beyond the establishment of the magnitudes resulting from measurements comprising the transition to different weighting scales of the test.

The algorithm begins by a reinitialization instruction after each basic analysis period TA or TB to describe it another time.

The establishment of the magnitudes Z, FC and RR is continuously carried out, on each basic period, these numbers or magnitudes are available at the end of each basic period TA and TB.

At the end of each of these periods, the algorithm is completely determined.

The algorithm is carried out anew each time that new values are available to establish a new overall probability.

At the end of two successive basic periods TA and TB, the two basic probabilities APFV or APFTV and PFV or PFTV are added in a summer to establish an overall probability which will determine a recognition state and will propose a decision to defibrillate.

The goal of the flow chart of the algorithm is to show the detail of these tests.

These tests are the three principal tests following: test of zeros, FC test, RR test for the variant, to which a ventricular tachycardia probability test (PTV test) is added for the actual complete procedure with improved embodiment.

This last test is transparent for a ventricular defibrillation, because the added value is null.

In contrast, this test increases the overall probability in different proportions according to the preceding criteria examined another time individually and taken into account simultaneously.

A new overall probability PGTV is in this manner defined which is the final probability after the examination of all of the criteria and the passage of all of the tests on two successive analysis basic periods TA and TB. It is equal to the sum of the two new elementary probabilities APFTV and PFTV which are the basic probabilities after the final test PTV:

$$PGTV = APFTV + PFTV$$

The rest of the general algorithm which is applicable as well to the basic embodiment and in the case of the improved embodiment implementing the fourth test in reference to FIGS. 18 and 19 will now be examined.

The goal of the first algorithm (FIG. 18) is to implement an ultimate test relative to the rapid ventricular tachycardia (FC greater than 140 b/mn) that is sought to be detected in the most certain manner possible.

The goal of the second algorithm (FIG. 19) is to monitor the case of an alarm and to determine if the alarm should be maintained or stopped if it has been triggered.

Concerning the first algorithm, the limit of the chosen probability, here the number 11, being exceeded, the case of an alarm is acquired. Before triggering the alarm, a last ventricular tachycardia test is carried out. This test concerns the two following alternatives:

1) the ventricular fibrillation probability FV is that of a case where RR is less or equal to 55% (low degree of arrythmia)
2) one interbeating duration in ten is longer than two seconds with a later passing of the control if the cardiac frequency is greater than 140 b/mn.

This last test has appeared to be necessary in the cases where it is certain that the probability of ventricular fibrillation is not large or in the case of an ineffectual detection of the QRS (the QRS complex is no longer recognized in the signal).

In this manner, if one or the other of the alternative conditions above:
  is met, the alarm is allowed to sound;
  is not met, it is determined whether the cardiac frequency is greater than 140 b/mn:
    if the cardiac frequency is less than this limit, the alarm is not validated and the algorithm returns to its beginning.
    if the cardiac frequency is greater than this limit, the alarm is triggered on this confirmation.

In the case of an alarm or of a detection in progress, the decision to maintain or to stop the alarm results from the algorithm represented in FIG. 19.

If over two successive measurement and analysis basic periods TA and TB, the probability is less than 5, the given alarm is then stopped and the algorithm proceeds as in FIG. 18.

In the contrary case, the alarm is maintained and the algorithm returns to the beginning of the general algorithm.

It is proper to note here that the measurements and analysis are periodically and continuously carried out. This means there is a constant monitoring. The least modification sensed by the detector according to the invention of the cardiac state of the patient will quasi instantaneously or not (depending on the result of the tests) modify the alarm state in which it finds itself.

It is also planned to carry out an additional and confirming analysis before the automatically triggering the alarm.

After taking the ECG signal on the patient, an amplification-filtering step is carried out followed by an analog preprocessing, an automatic gain control AGC and an analog/digital conversion in an ADC converter.

Concurrent to an analog preprocessing and AGC followed by ADC, the QRS complex is detected and a synchro QRS impulse is formed.

These informations, signals and data are entered in a microcalculator, for example of 8 bits, for various digital calculation and analysis processing with respect to the test on the values Z, FC, RR, test PTV, in view of emitting an alarm in the case of a recognition of the pathological cardiac condition and the systematic preparation of the defibrillation shock by the charging of the defibrillation capacitor of the associated fibrillator.

Figure 6:
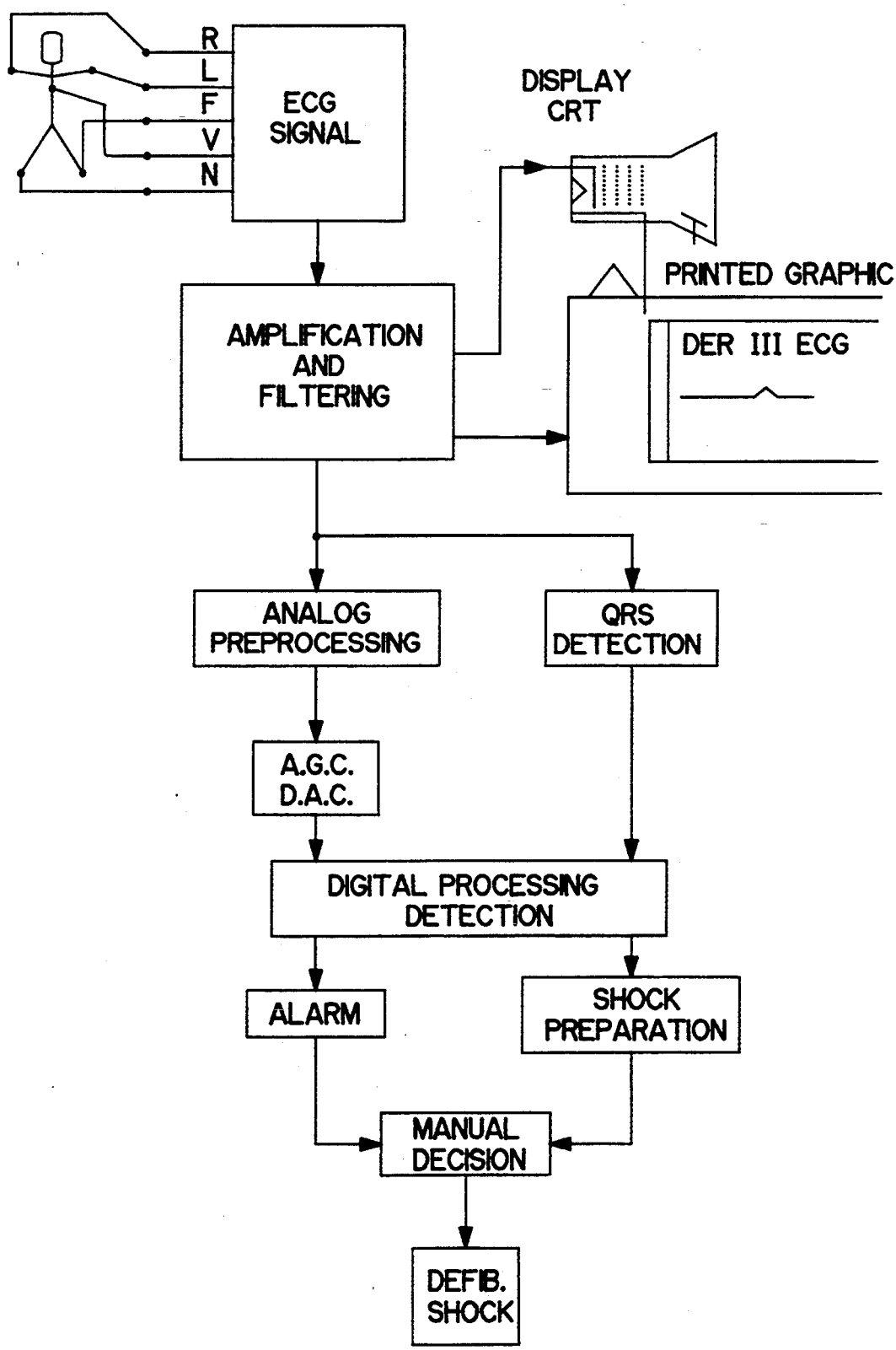
FIG. 6 is a synoptic diagram of the procedure to detect a hazardous pathological cardiac condition according to the basic embodiment of the invention.

According to the basic embodiment, the decision to shock belongs to the monitoring physician or equivalent personnel (FIG. 6).

Figure 7:
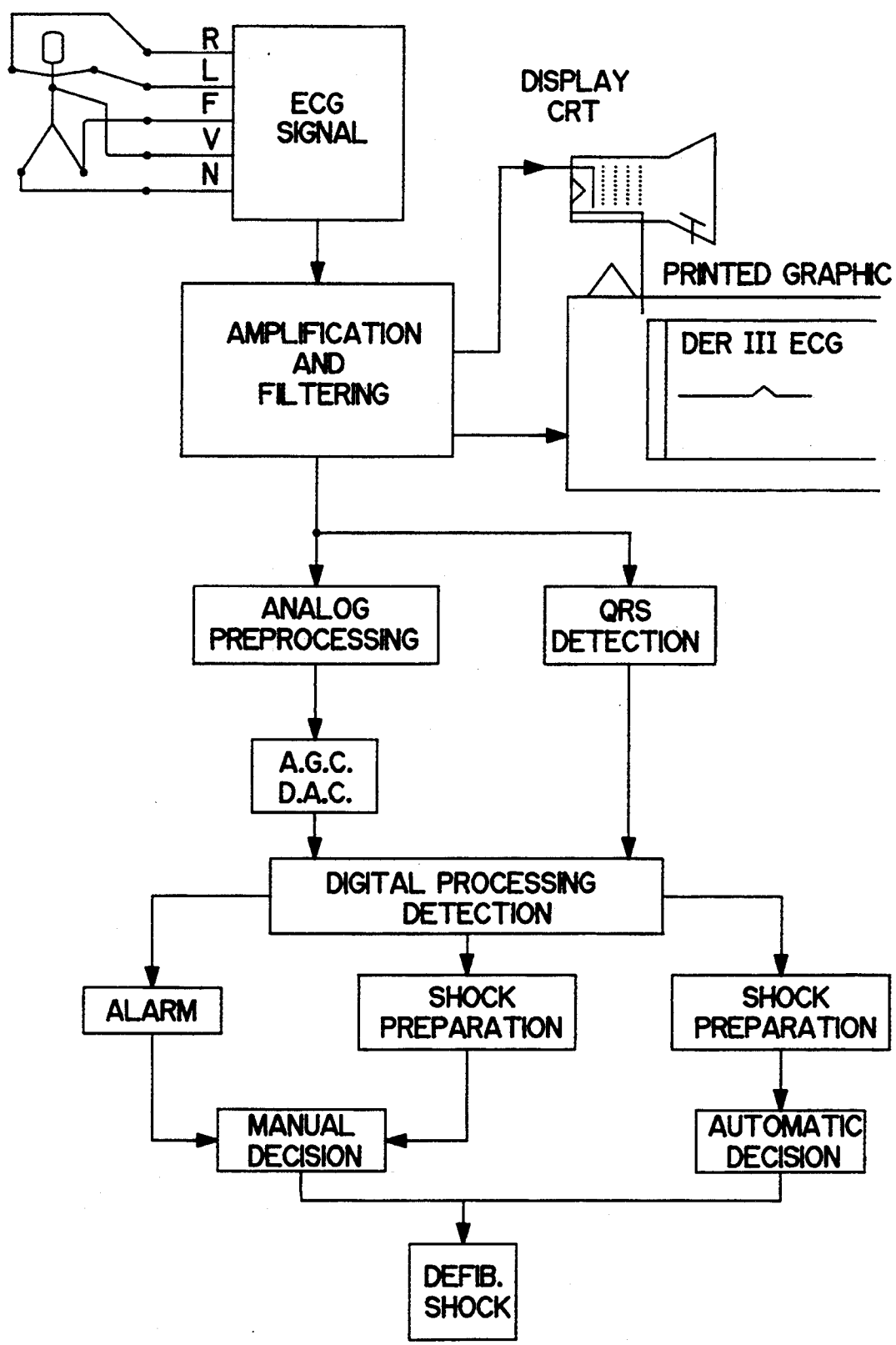
FIG. 7 is a synoptic diagram of the procedure to detect a hazardous pathological cardiac condition according to a basic embodiment improved by the automatic shock decision and an additional analysis.

According to a more complete embodiment, the decision to shock is automatically taken and given as soon as an additional analysis shows that the pathological state remains (FIG. 7).

The implementation means of the procedure will now be described with the aid of FIGS. 20 and 21.

The acquisition circuit receives the signals gathered by the electrodes placed on the patient.

The function of the acquisition circuit which may be a part of an existing monitor is to deliver from a signal superimposed with noise and parasitic signals, an ECG signal of 1 to 5 volts with a passband predefined by the limits from 0.05 to 100 Hz. The means used are conventionally and already utilized by other medical monitoring equipment.

A visualization by screen and a printer for the graphic version are a part of the acquisition circuit.

The detector itself according to the invention essentially comprises preprocessing means of the signal furnished by the acquisition circuit, digital preprocessing means and an alarm device.

Figure 20:
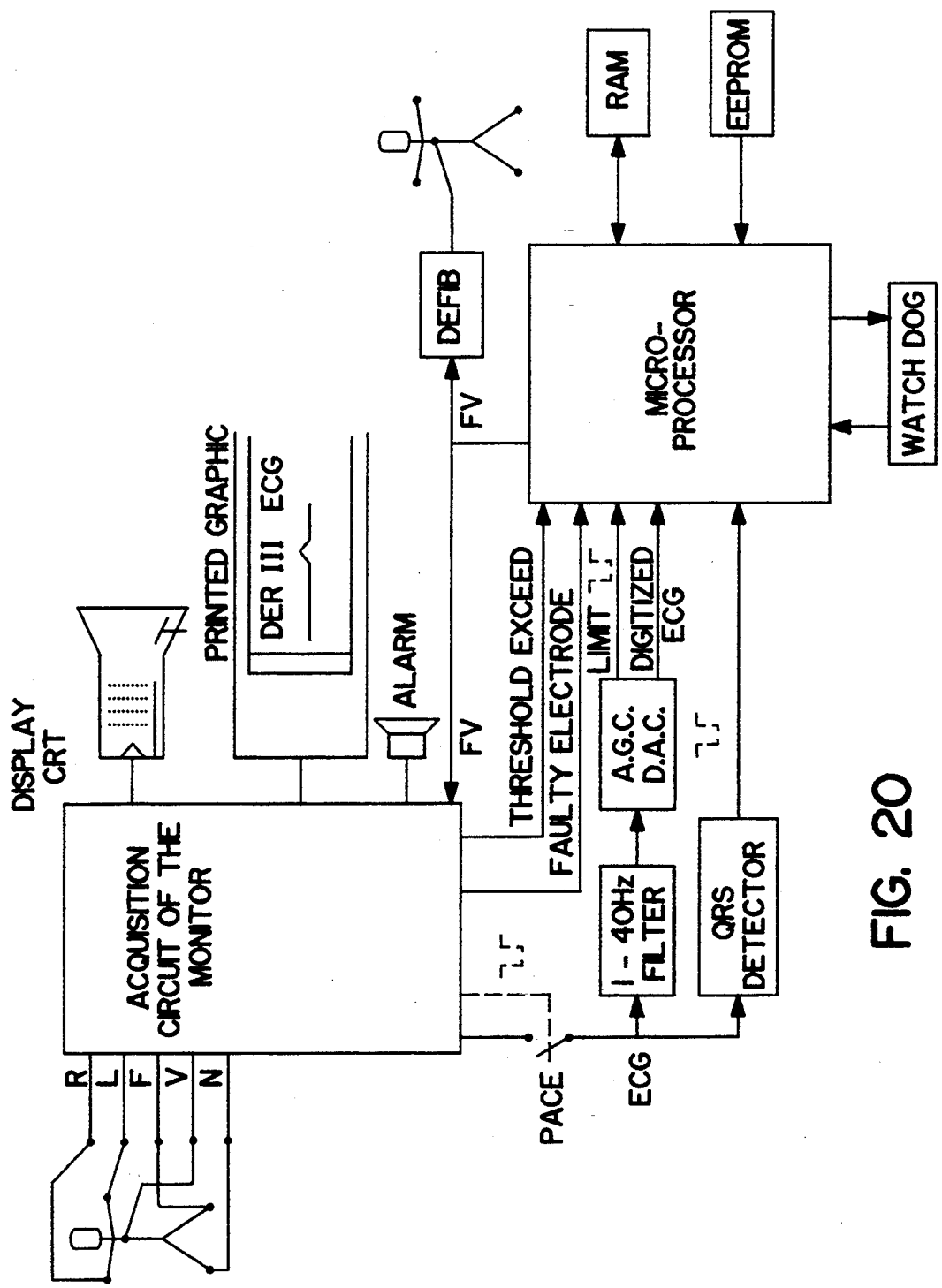
FIG. 20 is a functional synoptic diagram of the equipment implementing the procedure according to the invention.

The analog preprocessing means are composed of an analog-digital converter ADC preceded, in the embodiment represented in FIG. 20, by a filter whose filtering limits 1 and 40 Hz approximately, have been justified above. The goal of this filter is to allow the user to adapt the output pass band of the acquisition circuit to the input frequencies limited to 1 and 40 Hz of the analog-digital converter.

According to another embodiment, the standard acquisition circuit above may be replaced by an acquisition circuit delivering a signal whose pass band is already adapted, in this case, the preprocessing means would not comprise a filter. Eventually, one or several means to suppress the signals output from the detectors or equipment other than the ventricular fibrillation and ventricular tachycardia detectors according to the invention may be foreseen, which signals could perturb the ECG signal. As non-limiting example, a "switch" function to eliminate the impulses generated by a cardiac stimulator have been symbolically represented in FIG. 20 with the reference PACE.

The preprocessing means are essentially comprised of:
  a analog to digital converter abbreviated ADC
  an automatic gain control abbreviated AGC
  a peak signal value optimizer.

The peak signal detector is a conventional electronic circuit comprising a diode charging a peak value capacitor, if the amplitude of the preprocessed signal is larger than the amplitude charged in the capacitor. This capacitor is chosen with a ten millisecond charging constant to avoid taking into account a large amplitude parasitic signal and with a discharge time constant of several seconds (4 or 8 for example) to allow to follow the maximum of the signal if its amplitude diminishes.

The automatic gain controller AGC always allows the utilization of the full scale of the analog digital converter ADC. As specified, the absolute value of the maximum amplitude of the preprocessed analog signal has been chosen as conversion reference.

The processing means itself is based on a microprocessor, for example a microprocessor of the INTEL 8051 (8 bit) type utilized as microcalculator which necessitates few peripheral components: a frequency setting quartz oscillator, an EPROM containing the digital processing program, a working RAM memory and a "watchdog" autocontrol means. The digital processing program is that which has been described earlier for the procedure.

In parallel with the preprocessing means, a QRS complex detector is planned which is especially conceived to deliver to the microcalculator or to the digital processing unit a digital signal in synchronism with each QRS complex detected on the ECG of the patient.

Reference is now made to FIG. 21 for the description of the QRS complex detector.

A pass band filter of 18 Hz, of width 6 Hz eliminates the different components of the QRS complex. This complex may be positive or negative according to the derivation of the electrocardiogram, the rectifying means allowing to take into account the absolute value of the response of the pass band filter 18 Hz to always detect the first positive impulse.

The detection of the complex is then carried out with the aid of a comparator COMP by exceeding a threshold, which is variable, and depends on the maximum amplitude of the last detected QRS complex, of the elapsed time since this last QRS, and of a fixed value (which is a minimum detection value). A compromise has been found between these three data which are essentially charging and discharging times of the capacitor. The signal output from the comparator is a digital signal indicating the presence or absence of the QRS complex, it is then treated by a monostable vibrator, of refractory period on the order of 150 to 200 ms which prevents the double counting for the large complexes and which allows a synchronization signal up to cardiac frequencies greater than 300 pulsations per minute to be delivered.

According to an embodiment, the input signal of the QRS detector is taken at the input of the preprocessing filter. This arrangement is not limiting, as a signal originating from the adhesive defibrillation electrodes may be taken directly on the acquisition circuit.

The ventricular fibrillation and tachycardia detector additionally comprise:
  a technical alarm device to validate the alarm in the case of an anomaly in the acquisition circuit, preprocessing, or processing, for example, when an electrode has detached from the patient. This type of alarm is referenced in the figure by "electrode defect".

The alarm device itself consists in an audible alarm and/or a visual message managed for example by the acquisition circuit but validated by the output digital signal of the microcalculator.

For the semiautomatic embodiment of the detector, the digital output signal of the microcalculator also validates the charging means whose function is to place an associated defibrillator in a functioning state as soon as the operator gives it the command impulse. This embodiment is represented in dashed lines in FIG. 20.

We claim:

1. Procedure to monitor, detect, and to recognize a hazardous pathological cardiac condition in view of applying an electric defibrillation shock, wherein said procedure comprises the step of:
  a) acquiring an analog ECG signal from transducers attached to a patient's body;

b) processing said analog ECG signal in an analog preprocessing unit;

c) continuously sampling and digitizing said analog ECG signal over a measurement and analysis period D, said period D consisting of two identical basic periods TA and TB;

d) establishing from said digitized ECG signals values Z, FC and RR corresponding to results obtained by applying said digitized ECG signal to a zero test, a cardiac frequency test, and degree of arrythmia test, respectively;

e) forming, from said analog ECG signal, synchro QRS complex impulses when a cardiac rhythm of said patient exhibits QRS complexes;

f) digitally processing said Z, FC and RR values over two successive measurement analysis periods TA and TB;

g) obtaining, from said digitally processed Z, FC and RR values, a basic probability value for each basic period TA and TB, said basic probability value depending upon where said Z, FC and RR values fit within a weighting scale proper to each of said Z, FC and RR values;

h) summing said basic probability values obtained over said basic period TB with said basic probability value obtained over said previous basic period TA;

i) obtaining, from said summed basic probability values, an overall probability value;

j) repeating said steps a)–i) if said overall probability value does not exceed a set threshold;

k) triggering an emergency alarm and charging an electric defibrillator if said overall probability value equals or exceeds said threshold;

l) upon validation of said probability of recognition of a pathological cardiac condition, discharging said electric defibrillator onto said patient in an attempt to stabilize said cardiac rhythm.

2. Procedure according to claim 1, wherein said ECG signal is sampled at a sampling frequency of 250 Hz and each measurement and analysis period TA and TB is 4 seconds.

3. Procedure according to claim 1, wherein said synchro QRS impulse is formed by:
inputting said ECG signal into an amplified filter having a 100 Hz cutoff frequency;
inputting an output of said amplified filter into a bandpass filter centered on 18 Hz;
isolating an absolute value of an output of said bandpass filter;
comparing said absolute value to a variable threshold, a peak amplitude of a last detected QRS complex, and a fixed, minimum detection value;
outputting from said comparator a synchro QRS impulse calibrated in amplitude and in duration, said synchro QRS impulse indicating a presence or absence of said QRS complex in said cardiac rhythm of said patient.

4. Procedure according to claim 1, wherein said Z values are defined as a percentage of a number of sampled points during a measurement and analysis period whose voltage level is located within 20% of a maximum voltage level of said ECG signal with respect to a total number of sampled points less than 50% of the total number, and establishing a probability value by allocating to said Z values, through a probability scale of a test of zeros, a variable weighting coefficient equal to:

4 if said Z value during said measurement and analysis period is located between 0% and 50%;

2 if said Z value during said measurement and analysis period is located between 50% and 55%;

1 if said Z value during said measurement and analysis period is located between 55% and 70%;

0 if said Z value during said measurement and analysis period is located between 70% and 100%;

3 if said number Z during said measurement and analysis period is above 100%.

5. Procedure according to claim 1, wherein said FC values of cardiac frequency are defined by the following formula:

$$FC = 60 \times (N+1)/(T+2)$$

wherein, $N$ = number of synchro QRS impulses counted during a reference period;

$T$ = duration between an end of said reference period and a next synchro QRS impulse;

and wherein a basic probability value is established by allocating to said FC value, by a probability scale of said cardiac frequency FC test, a variable weighting coefficient equal to:

0 if said cardiac frequency during said measurement and analysis period is less than 140 beats per minute, thus indicating a null probability;

1 if said cardiac frequency during said measurement and analysis period is located between 140 and 200 beats per minute, thus indicating a weak probability;

2 if said cardiac frequency during said measurement and analysis period is located between 200 and 300 beats per minute, thus indicating an average probability;

3 if said cardiac frequency during said measurement and analysis period is above 300 beats per minute, thus indicating a strong probability.

6. Procedure according to claim 1, wherein said RR values of degree of arrythmia are defined as being a relation in percentage points between a number of interbeatings in ten from a test last interbeatings which are located at + or −30% of an average interbeating value Ti, and wherein a basic probability is established by allocating to said value RR, through a weighting scale of said arrhythmia test RR, a variable weighting coefficient equal to:

3 if said degree of arrhythmia RR during said measurement and analysis period is less than or equal to 50%;

2 if said degree of arrhythmia RR during said measurement and analysis period is located between 55% and 65%;

1 if said degree of arrhythmia RR during said measurement and analysis period is located between 65% and 75%;

0 if said degree of arrhythmia RR during said measurement and analysis period is located between 75% and 100%.

7. Procedure according to claim 1, wherein an additional ventricular tachycardia probability PTV is established according to which an additional probability weight is added if the following conditions are simultaneously met:

a possibility of ventricular fibrillation is such that said RR value is less than or equal to 55%;

one interbeating time Ti in ten is greater than 2 seconds.

8. Procedure according to claim 1, wherein when said emergency alarm is triggered, said procedure further proceeds to carry out a final test comprising the steps of:
- verifying that the degree of arrhythmia is less than or equal to 55%;
- if said interbeating time is greater than at least 2 seconds, validating said emergency alarm if a positive response is obtained and also validating said emergency alarm if a negative response is obtained and said cardiac frequency is greater than 140 beats per minute.

9. Procedure according to claim 1, wherein said emergency alarm is maintained if said basic probabilities over two successive basic periods TA and TB are each less than 5.

10. Procedure according to claim 1, wherein said electric defibrillator is automatically put in a condition of readiness to apply a defibrillation electric shock as soon as said overall probability value exceeds said set threshold.

* * * * *